(12) United States Patent
Dempsey

(10) Patent No.: US 9,572,999 B2
(45) Date of Patent: *Feb. 21, 2017

(54) SYSTEM FOR DELIVERING CONFORMAL RADIATION THERAPY WHILE SIMULTANEOUSLY IMAGING SOFT TISSUE

(71) Applicant: University of Florida Research Foundation, Inc., Gainesville, FL (US)

(72) Inventor: James F. Dempsey, Chagrin Falls, OH (US)

(73) Assignee: University of Florida Research Foundation, Inc., Gainesville, FL (US)

(*) Notice: Subject to any disclaimer, the term of this patent is extended or adjusted under 35 U.S.C. 154(b) by 0 days.

This patent is subject to a terminal disclaimer.

(21) Appl. No.: 14/807,857

(22) Filed: Jul. 23, 2015

(65) Prior Publication Data

US 2016/0184609 A1 Jun. 30, 2016

Related U.S. Application Data

(63) Continuation of application No. 13/783,084, filed on Mar. 1, 2013, now Pat. No. 9,114,253, which is a continuation of application No. 13/195,618, filed on Aug. 1, 2011, now abandoned, which is a continuation of application No. 12/609,953, filed on Oct. 30, 2009, now Pat. No. 8,190,233, which is a continuation of application No. 11/059,914, filed on Feb. 17, 2005, now Pat. No. 7,907,987.

(60) Provisional application No. 60/546,670, filed on Feb. 20, 2004.

(51) Int. Cl.
| | |
|---|---|
| *A61N 5/00* | (2006.01) |
| *A61N 5/10* | (2006.01) |
| *A61B 5/055* | (2006.01) |
| *G01R 33/381* | (2006.01) |
| *G01R 33/48* | (2006.01) |
| *A61B 5/00* | (2006.01) |

(52) U.S. Cl.
CPC ............ *A61N 5/1064* (2013.01); *A61B 5/055* (2013.01); *A61B 5/4836* (2013.01); *A61B 5/4848* (2013.01); *A61N 5/1042* (2013.01); *A61N 5/1049* (2013.01); *A61N 5/1077* (2013.01); *A61N 5/1081* (2013.01); *G01R 33/381* (2013.01); *G01R 33/4808* (2013.01); *A61B 5/4504* (2013.01); *A61N 5/1037* (2013.01); *A61N 5/1067* (2013.01); *A61N 2005/1055* (2013.01); *G01R 33/4812* (2013.01)

(58) Field of Classification Search
CPC .... A61N 5/1064; A61N 5/1077; A61B 5/055; A61B 5/4836
See application file for complete search history.

*Primary Examiner* — Joseph M Santos Rodriguez
(74) *Attorney, Agent, or Firm* — Mintz Levin Cohn Ferris Glovsky and Popeo, P.C.

(57) ABSTRACT

Devices and processes for performing magnetic resonance imaging of the anatomy of a patient during radiation therapy to measure and control the radiation dose delivered to the patient.

14 Claims, 12 Drawing Sheets

SYSTEM FOR DELIVERING CONFORMAL RADIATION THERAPY WHILE SIMULTANEOUSLY IMAGING SOFT TISSUE

CROSS-REFERENCE TO RELATED APPLICATIONS

This application is a continuation of application Ser. No. 13/783,084 filed Mar. 1, 2013, now U.S. Pat. No. 9,114,253; which is a continuation application of U.S. application Ser. No. 13/195,618 filed on Aug. 1, 2011, which is a continuation of U.S. application Ser. No. 12/609,953 filed on Oct. 30, 2009, now U.S. Pat. No. 8,190,233, which is a continuation of U.S. application Ser. No. 11/059,914 filed Feb. 17, 2005, now U.S. Pat. No. 7,907,987, which claims the benefit of Provisional application 60/546,670 filed Feb. 20, 2004, the entirety of which are incorporated by reference herein.

FIELD OF THE INVENTION

This invention relates to a radiotherapy system and method, more particularly a radiotherapy system and method for rapidly and repeatedly imaging the anatomy of a patient during the moments that dose is delivered to the patient during radiation therapy so that the actual ionizing radiation dose delivered to the patient in portions over a course of many days or weeks may be determined and the therapy may be adjusted to account for any treatment delivery errors caused by organ motions or changes in patient geometry. The magnetic resonance imaging method employed in this invention also improves the soft tissue contrast over the existing x-ray computed tomography (CT) imaging and may provide additional metabolic and physiological information to improve target delineation and allow for the monitoring of the response of the patient or disease to therapy.

BACKGROUND OF THE INVENTION

In treating disease caused by proliferative tissue disorders such as cancer and coronary artery restenosis with radiation, the portions of the patient known to contain or suspected to contain disease are irradiated. For this purpose, a radiotherapy planning system is used to first acquire planning images of the diseased portion(s) and surrounding regions.

Radiotherapy planning systems generally include a CT or magnetic resonance imaging (MRI) simulator. CT or MRI radiography is carried out on a single day before the beginning of therapy to acquire a plurality of coregistered sectional 2-D images. These sectional images are combined using known algorithms to produce 3-D images. These 3-D simulation images are displayed and then analyzed to identify the location of regions of suspected disease to be treated, such as a radiographically evident tumor or regions suspected of microscopic disease spread. These regions to be treated are called radiotherapy targets. In order to attempt to account for organ motions, the concept of margins and planning target volumes (PTVs) was developed to attempt to irradiate a volume that would hopefully contain the target during most of the irradiation. PTVs include a geometric margin to account for variations in patient geometry or motion. Likewise, the 3-D simulation images are displayed and then analyzed to identify important normal anatomy and tissues that may be damaged by the radiation, such as the spinal cord and lung, to evaluate the potential impact of radiation on the function of these tissues. These regions to be spared or protected from excessive radiation are called critical structures or organs at risk and may also include a margin to account for variations in patient geometry or motion. The delivery of radiation therapy is then traditionally planned on a single static model of radiotherapy targets and critical structures derived from a single set of CT and/or MRI images. Because the known art does not allow for simultaneous imaging and therapy, the patient and all of their internal organs need to be repositioned exactly for accurate dose delivery. However, it is known in the art that exactly repositioning the patient even for a single delivery of dose is not possible due to several factors including: the inability to reproduce the patient setup, i.e., the geometry and alignment of the patient's body; physiological changes in the patient, such as weight loss or tumor growth and shrinkage; and organ motions in the patients including but not limited to breathing motion, cardiac motion, rectal distension, peristalsis, bladder filling, and voluntary muscular motion. Note that the organ motions may occur on rapid time scales such that changes may occur during a single dose delivery (e.g., breathing motion), termed "intra-fraction" organ motions, or they may occur on slower time scales such that changes occur in between dose deliveries, termed "inter-fraction" organ motions. Much of the curative treatment of patients with cancer outside the cranium requires the delivered radiation therapy to be fractionated, i.e., the dose is delivered in many fractions. Typically, dose is delivered in single 1.8 to 2.2 Gy fractions or double 1.2 to 1.5 Gy fractions daily, and delivered during the work week (Monday through Friday); taking 7 to 8 weeks to deliver, e.g., a cumulative dose of 70 to 72 Gy at 2.0 or 1.8 Gy, respectively. A purpose of this invention is to overcome the limitations imposed on radiation therapy by patient setup errors, physiological changes, and both intra- and inter-fraction organ motions throughout the many weeks of radiation therapy. Another purpose is to allow the physician to periodically monitor the response of the patient's disease to the therapy by performing MRI that provides metabolic and physiological information or assessing the growth or shrinkage of gross disease.

An irradiation field shape is then determined to coincide with an outline of an image of the target's diseased regions or suspected regions appearing in the planning images. An irradiating angle is determined from sectional images of a wide region including the diseased portion or a transmitted image, seen from a particular direction, produced by the 3-D simulation images. A transmitted image seen from the irradiating angle is displayed. The operator then determines a shape of an irradiation field on the image displayed, and sets an isocenter (reference point) to the irradiation field.

Optionally, the patient may be positioned relative to a conventional simulator (ortho-voltage X-ray imaging system that allows portal images to be generated for radiation therapy setup). An irradiating angle corresponding to the irradiating angle determined as above is set to the simulator, and an image is generally radiographed on a film through radiography for use as a reference radiograph. Similar digitally reconstructed radiographs may be produced using CT or MRI simulation software.

The patient is then positioned and restrained relative to a radiation treating apparatus which generally includes a radiation source, typically a linear accelerator. An irradiating angle is set to the irradiating angle determined as above, and film radiography is carried out by emitting radiation from the radiation treating apparatus. This radiation film image is correlated with the above film image acting as the reference radiograph to confirm that the patient has been positioned according to plan as correctly as possible before proceeding with radiotherapy. Some repositioning is generally required to place the patient such that the structures in the reference radiograph match the structures in the treatment radiograph to within a tolerance of 0.2 to 0.5 cm. After acceptable patient positioning is confirmed, radiotherapy is begun.

Patient setup errors, physiological changes, and organ motions result in increasing misalignment of the treatment beams relative to the radiotherapy targets and critical structures of a patient as the radiotherapy process proceeds. For years practitioners have been acquiring hard-copy films of the patient using the radiation therapy beam, technically referred to as a "port film" to attempt to ensure that the beam position does not significantly vary from the original plan. However, the port films acquired are generally only single 2-D projection images taken at some predetermined interval during the radiotherapy process (typically 1 week). Port films cannot account for organ motion. Additionally, port films do not image soft tissue anatomy with any significant contrast and only provide reliable information on the boney anatomy of the patient. Accordingly, misalignment information is only provided at the instants in time in which the port images are taken and may be misleading as the boney anatomy and soft tissue anatomy alignment need not correlate and change with time. With appropriate markers in the port image provided, the beam misalignment may be determined and then corrected to some limited degree.

More recently, some have disclosed acquiring the port images electronically, referred to as electronic portal imaging. This imaging technique employs solid state semiconductor, scintillator, or liquid ionization chamber array technology to capture x-ray transmission radiographs of the patient using the x-rays of the linear accelerator or an associated kilovoltage x-ray unit. As with the hard-copy technique, misalignment data is only provided at the instants in time in which the port images are taken. Another recent advance in electronic portal imaging includes the use of implanted interstitial radio-opaque markers that attempt to image the location of soft tissues. These procedures are invasive and subject to marker migration. Even when performed with the rapid acquisition of many images, it only finds the motion of discrete points identified by the radio-opaque markers inside a soft tissue and cannot account for the true complexities of organ motions and the dosimetric errors that they cause. Another recent advance, that creates 3D volumetric image sets from many 2D electronic portal images, is the acquisition of volumetric cone-beam x-ray CT or helical tomotherapy megavoltage x-ray CT image set before or after the daily delivery of therapy. While this technology may account for patient setup errors, i.e., the geometry and alignment of the patient's body, physiological changes in the patient, such as weight loss or tumor growth and shrinkage, and inter-fraction organ motions in the patient, such as rectal filling and voiding; it cannot account for intra-fraction organ motions in the patients. Intrafraction organ motions are very important and include, but are not limited to, breathing motion, cardiac motion, rectal gas distension, peristalsis, bladder filling, and voluntary muscular motion.

Radiation therapy has historically been delivered to large regions of the body including the target volume. While some volume margin is required to account for the possibility of microscopic disease spread, much of the margin is required to account for uncertainties in treatment planning and delivery of radiation. Reducing the total volume of tissue irradiated is beneficial, since this reduces the amount of normal tissue irradiated and therefore reduces the overall toxicity to the patient from radiation therapy. Furthermore, reduction in overall treatment volume may allow dose escalation to the target, thus increasing the probability of tumor control.

Clinical cobalt ($Co^{60}$ radioisotope source) therapy units and MV linear accelerators (or linacs) were introduced nearly contemporaneously in the early 1950's. The first two clinical cobalt therapy units were installed nearly simultaneously in October of 1951 in Saskatoon and London, Ontario. The first MV linear accelerator installed solely for clinical use was at Hammersmith Hospital, London England in June of 1952. The first patient was treated with this machine in August of 1953. These devices soon became widely employed in cancer therapy. The deeply penetrating ionizing photon beams quickly became the mainstay of radiation therapy, allowing the widespread noninvasive treatment of deep seated tumors. The role of X-ray therapy slowly changed with the advent of these devices from a mainly palliative therapy to a definitive curative therapy. Despite similarities, cobalt units and linacs were always viewed as rival technologies in external beam radiotherapy. This rivalry would result in the eventual dominance of linacs in the United States and Western Europe. The cobalt unit was quite simplistic and was not technically improved significantly over time. Of course, the simplicity of the cobalt unit was a cause for some of its appeal; the cobalt units were very reliable, precise, and required little maintenance and technical expertise to run. Early on, this allowed cobalt therapy to become the most widespread form of external beam therapy. The linac was the more technically intensive device. Accelerating high currents of electrons to energies between 4 and 25 MeV to produce beams of bremsstrahlung photons or scattered electrons, the linac was a much more versatile machine that allowed more penetrating beams with sharper penumbrae and higher dose rates. As the linac became more reliable, the benefits of having more penetrating photon beams coupled with the addition of electron beams was seen as strong enough impetus to replace the existing cobalt units. Cobalt therapy did not die away without some protests and the essence of this debate was captured in a famous paper in 1986 by Laughlin, Mohan, and Kutcher which explained the pros and cons of cobalt units with linacs. This was accompanied by an editorial from Suit that pleaded for the continuance and further technical development of cobalt units. The pros of cobalt units and linacs have already been listed. The cons of cobalt units were seen as less penetrating depth dose, larger penumbra due to source size, large surface doses for large fields due to lower energy contamination electrons, and mandatory regulatory oversight. The cons for linacs increased with their increasing energy (and hence their difference from a low energy cobalt beam), and were seen to be increased builddown, increased penumbra due to electron transport, increased dose to bone (due to increased dose due to pair production), and most importantly the production of photo-neutrons at acceleration potentials over 10 MV.

In the era before intensity modulated radiation therapy (IMRT), the linac held definite advantages over cobalt therapy. The fact that one could produce a very similar beam to cobalt using a 4 MV linac accelerating potential combined with the linac's ability to produce either electron beams or more penetrating photon beams made the linac preferable. When the value of cobalt therapy was being weighed against the value linac therapy, radiation fields were only manually developed and were without the benefit of IMRT. As IMRT has developed, the use of higher MV linac accelerating potential beams and electron beams have been largely abandoned by the community. This is partly due to the increased concern over neutron production (and increased patient whole body dose) for the increased beam-on times required by IMRT and the complexity of optimizing electron beams, but most importantly because low MV photon-beam IMRT could produce treatment plans of excellent quality for all sites of cancer treatment.

IMRT represents a culmination of decades of improving 3D dose calculations and optimization to the point that we have achieved a high degree of accuracy and precision for static objects. However, there is a fundamental flaw in our currently accepted paradigm for dose modeling. The problem lies with the fact that patients are essentially dynamic deformable objects that we cannot and will not perfectly reposition for fractioned radiotherapy. Even for one dose delivery, intra-fraction organ motion can cause significant errors. Despite this fact, the delivery of radiation therapy is traditionally planned on a static model of radiotherapy targets and critical structures. The real problem lies in the fact that outside of the cranium (i.e., excluding the treatment of CNS disease using Stereotactic radiotherapy) radiation therapy needs to be fractionated to be effective, i.e., it must be delivered in single 1.8 to 2.2 Gy fractions or double 1.2 to 1.5 Gy fractions daily, and is traditionally delivered during the work week (Monday through Friday); taking 7 to 8 weeks to deliver a curative dose of 70 to 72 Gy at 2.0 or 1.8 Gy, respectively. This daily fractionation requires the patient and all of their internal organs to be repositioned exactly for accurate dose delivery. This raises an extremely important question for radiation therapy: "Of what use is all of the elegant dose computation and optimization we have developed if the targets and critical structures move around during the actual therapy?" Recent critical reviews of organ motion studies have summarized the existing literature up to 2001 and have shown that the two most prevalent types of organ-motion: patient set-up errors and organ motions. While significant physiological changes in the patient do occur, e.g., significant tumor shrinkage in head-and-neck cancer is often observed clinically, they have not been well studied. Organ motion studies have been further subdivided into inter-fraction and intra-fraction organ motion, with the acknowledgement that the two cannot be explicitly separated, i.e., intra-fraction motions obviously confound the clean observation of inter-fraction motions. Data on inter-fraction motion of gynecological tumors, prostate, bladder, and rectum have been published, as well as data on the intra-fraction movement of the liver, diaphragm, kidneys, pancreas, lung tumors, and prostate. Many peer-reviewed publications, spanning the two decades prior to publication have demonstrated the fact that both inter- and intra-fraction organ motions may have a significant effect on radiation therapy dosimetry. This may be seen in the fact that displacements between 0.5 and 4.0 cm have been commonly observed in studies of less than 50 patients. The mean displacements for many observations of an organ motion may be small, but even an infrequent yet large displacement may significantly alter the biologically effective dose received by a patient, as it is well accepted that the correct dose per fraction must be maintained to effect tumor control. In a more focused review of intra-fraction organ motion recently published by Goitein (Seminar in Radiation Oncology 2004 January; 14(1):2-9), the importance of dealing with organ motion related dosimetry errors was concisely stated: " . . . it is incontestable that unacceptably, or at least undesirably, large motions may occur in some patients . . . " It was further explained by Goitein that the problem of organ motions has always been a concern in radiation therapy: "We have known that patients move and breathe and that their hearts beat and their intestines wriggle since radiation was first used in cancer therapy. In not-so-distant decades, our solution was simply to watch all that motion on the simulator's fluoroscope and then set the field edge wires wide enough that the target (never mind that we could not see it) stayed within the field."

In an attempt to address the limitations imposed on radiation therapy by patient setup errors, physiological changes, and organ motion throughout the protracted weeks of radiation therapy, the prior art has been advanced to imaging systems capable of acquiring a volumetric CT "snap shot" before and after each delivery of radiation. This new combination of radiation therapy unit with radiology imaging equipment has been termed image-guided radiation therapy (IGRT), or preferably image guided IMRT (IG-IMRT). The prior art has the potential for removing patient setup errors, slow physiological changes, and inter-fraction organ motions that occur over the extended course of radiation therapy. However, the prior art cannot account for intra-fraction organ motion which is a very significant form of organ motion. The prior art devices are only being used to shift the gross patient position. The prior art cannot capture intra-fraction organ motion and is limited by the speed at which helical or cone-beam CT imaging may be performed. Secondly, but perhaps equally important, CT imaging adds to the ionizing radiation dose delivered to the patient. It is well known that the incidence of secondary carcinogenesis occurs in regions of low-to-moderate dose and the whole body dose will be increased by the application of many CT image studies.

CT imaging and MRI units were both demonstrated in the 1970's. CT imaging was adopted as the "gold standard" for radiation therapy imaging early on due to its intrinsic spatial integrity, which comes from the physical process of X-ray attenuation. Despite the possibility of spatial distortions occurring in MRI, it is still very attractive as an imaging modality for radiotherapy as it has a much better soft tissue contrast than CT imaging and the ability to image physiological and metabolic information such as chemical tumor signals or oxygenation levels. The MRI artifacts that influence the spatial integrity of the data are related to undesired fluctuations in the magnetic field homogeneity and may be separated into two categories: 1) artifacts due to the scanner such as field inhomogeneities intrinsic to the magnet design and induced eddy currents due to gradient switching; and 2) artifacts due to the imaging subject, i.e., the intrinsic magnetic susceptibility of the patient. Modern MRI units are carefully characterized and employ reconstruction algorithms that may effectively eliminate artifacts due to the scanner. At high magnetic field strength, in the range of 1.0-3.0 T, magnetic susceptibility of the patient may produce significant distortions (which are proportional to field strength) that may often be eliminated by first acquiring susceptibility imaging data. Recently, many academic centers have started to employ MRI for radiation therapy treatment planning Rather than dealing with patient related artifacts at high field, many radiation therapy centers have employed low field MRI units with 0.2-0.3 T for radiation therapy treatment planning, as these units diminish patient-susceptibility spatial distortions to insignificant levels. For dealing with intra-fraction organ motion MRI is highly favorable due to the fact that it is fast enough to track patient motions in real-time, has an easily adjustable and orientable field of view, and does not deliver any additional ionizing radiation to the patient which may increase the incidence of secondary carcinogenesis. Breath controlled and spirometer-gated fast multi-slice CT has recently been employed in an attempt to assess or model intra-fraction breathing motion by many research groups. Fast, single-slice MRI has also been employed in the assessment of intra-fraction motions, and dynamic parallel MRI is able to perform volumetric intra-fraction motion imaging. MRI holds a definite advantage over CT for fast repetitive imaging due to the need for CT imaging to deliver increasing doses to the patient. Concerns over increased secondary carcinogenesis due to whole-body dose already exist for IMRT and become significantly worse with the addition of repeated CT imaging.

In the prior art, two research groups appear to have simultaneously been attempting to develop a MRI unit integrated with a linac. In 2001, a patent was filed by Green which teaches an integrated MRI and linac device. In 2003, a group from the University of Utrecht in the Netherlands presented their design for an integrated MRI and linac device and has since reported dosimetric computations to test the feasibility of their device. The significant difficulty with integrating a MRI unit with a linac as opposed to a CT imaging unit, is that the magnetic field of the MRI unit makes the linac inoperable. It is well known that a charged particle moving at a velocity, $\overline{V}$, in the presence of a magnetic field, $\overline{B}$, experiences a Lorentz force given by $\overline{F}=q(\overline{v}\times\overline{B})$. The Lorentz force caused by the MRI unit will not allow electrons to be accelerated by the linac as they cannot travel in a linear path, effectively shutting the linac off. The high radiofrequency (RF) emittance of the linac will also cause problems with the RF transceiver system of the MRI unit, corrupting the signals required for image reconstruction and possibly destroying delicate circuitry. The integration of a linac with a MRI unit is a monumental engineering effort and has not been enabled.

Intensity modulated radiation therapy (IMRT) is a type of external beam treatment that is able to conform radiation to the size, shape and location of a tumor. IMRT is a major improvement as compared to conventional radiation treatment. The radiotherapy delivery method of IMRT is known in the art of radiation therapy and is described in a book by Steve Webb entitled "Intensity-Modulated Radiation Therapy" (IOP Publishing, 2001, ISBN 0750306998). This work of Webb is incorporated by reference into the application in its entirety and hereafter referred to as "Webb 2001". The effectiveness of conventional radiation therapy is limited by imperfect targeting of tumors and insufficient radiation dosing. Because of these limitations, conventional radiation may expose excessive amounts of healthy tissue to radiation, thus causing negative side-effects or complications. With IMRT, the optimal 3D dose distribution, as defined by criteria known in the art (Webb 2001), is delivered to the tumor and dose to surrounding healthy tissue is minimized.

In a typical IMRT treatment procedure, the patient undergoes treatment planning x-ray CT imaging simulation with the possible addition of MRI simulation or a position emission tomography (PET) study to obtain metabolic information for disease targeting. When scanning takes place, the patient is immobilized in a manner consistent with treatment so that the imaging is completed with the highest degree of accuracy. A radiation oncologist or other affiliated health care professional typically analyzes these images and determines the 3D regions that need to be treated and 3D regions that need to be spared, such as critical structures, e.g. the spinal cord and surrounding organs. Based on this analysis, an IMRT treatment plan is developed using large-scale optimization.

IMRT relies on two advanced technologies. The first is inverse treatment planning Through sophisticated algorithms using high speed computers an acceptable treatment plan is determined using an optimization process which is intended to deliver a prescribed uniform dose to the tumor while minimizing excessive exposure to surrounding healthy tissue. During inverse planning a large number (e.g. several thousands) of pencil beams or beamlets which comprise the radiation beam are independently targeted to the tumor or other target structure with high accuracy. Through optimization algorithms the non-uniform intensity distributions of the individual beamlets are determined to attain certain specific clinical objectives.

The second technology comprising IMRT generally utilizes multi-leaf collimators (MLC). This technology delivers the treatment plan derived from the inverse treatment planning system. A separate optimization called leaf sequencing is used to convert the set of beamlet fluences to an equivalent set of leaf motion instructions or static apertures with associated fluences. The MLC is typically composed of computer-controlled tungsten leaves that shift to form specific patterns, blocking the radiation beams according to the intensity profile from the treatment plan. As an alternative to MLC delivery, an attenuating filter may also be designed to match the fluence of beamlets. The current invention contemplates the fact that MLC delivery is capable of adjusting a delivery rapidly to account for intra-fraction organ motions while an attenuating filter cannot be actively adjusted.

After the plan is generated and quality control checking has been completed, the patient is immobilized and positioned on the treatment couch attempting to reproduce the positioning performed for the initial x-ray CT or magnetic resonance imaging. Radiation is then delivered to the patient via the MLC instructions or attenuation filter. This process is then repeated for many work weeks until the prescribed cumulative dose is assumed to be delivered.

Magnetic resonance imaging (MRI) is an advanced diagnostic imaging procedure that creates detailed images of internal bodily structures without the use of ionizing radiation, which is used in x-ray or megavoltage x-ray CT imaging. The diagnostic imaging method of MRI is known in the arts of radiology and radiation therapy and is described in the books by E. M. Haacke, R. W. Brown, M. R. Thompson, R. Venkatesan entitled Magnetic Resonance Imaging: Physical Principles and Sequence Design (John Wiley & Sons, 1999, ISBN 0-471, 35128-8) and by Z.-P. Liang and P. C. Lauterbur entitled Principles of Magnetic Resonance Imaging: A Signal Processing Perspective. (IEEE Press 2000, ISBN 0-7803-4723-4). These works of Haacke et al. and Liang and Lauterbur are incorporated by reference into the application in their entirety and hereafter referred to as "Haacke et al. 1999" and "Liang and Lauterbur 2001", respectively. MRI is able to produce detailed images through the use of a powerful main magnet, magnetic field gradient system, radiofrequency (RF) transceiver system, and an image reconstruction computer system. Open Magnetic Resonance Imaging (Open MRI) is an advanced form of MRI diagnostic imaging that uses a main magnet geometry which does not completely enclose the patient during imaging. MRI is a very attractive imaging modality for radiotherapy as it has a much better soft tissue contrast than CT imaging and the ability to image physiological and metabolic information such as spectroscopic chemical tumor signals or oxygenation levels. Many tracer agents exist and are under development for MRI to improve soft tissue contrast (e.g. Gadopentate dimeglumine for kidney or bowel enhancement, or Gadoterate meglumine for general contrast). Novel contrast agents are currently under development that will allow for the metabolic detection of tumors similar to PET imaging by employing either hyperpolarized liquids containing carbon 13, nitrogen 15, or similar stable isotopic agents or paramagnetic niosomes. All of these diagnostic MRI techniques enhance the accurate targeting of disease and help assess response to treatment in radiation therapy.

CT scanning for IMRT treatment planning is performed using thin sections (2-3 mm), sometimes after intravenous injection of an iodine-containing contrast medium and filmed at soft tissue and bone window and level settings. It has the advantage of being more widely available, cheaper than magnetic resonance imaging (MRI) and it may be calibrated to yield electron density information for treatment planning Some patients who cannot be examined by MRI (due to claustrophobia, cardiac pacemaker, aneurism clips, etc.) may be scanned by CT.

The problem of patient setup errors, physiological changes, and organ motions during radiotherapy is currently a topic of great interest and significance in the field of radiation oncology. It is well know that the accuracy of conformal radiation therapy is significantly limited by changes in patient mass, location, orientation, articulated geometric configuration, and inter-fraction and intra-fraction organ motions (e.g. during respiration), both during a single delivery of dose (intrafraction changes, e.g., organ motions such as rectal distension by gas, bladder filling with urine, or thoracic breathing motion) and between daily dose deliveries (interfraction changes, e.g., physiological changes such as weight gain and tumor growth or shrinkage, and patient geometry changes). With the exception of the subject invention, no single effective method is known to account for all of these deviations simultaneously during each and every actual dose delivery. Current state-of-the-art imaging technology allows taking 2D and 3D megavoltage and orthovoltage x-ray CT "snap-shots" of patients before and after radiation delivery or may take time resolved 2D radiographs which have no soft tissue contrast during radiation delivery.

Great advances have been made in conformal radiation therapy; however, their true efficacy is not realized without complete real-time imaging guidance and control provided by the present invention. By the term "real-time imaging" we mean repetitive imaging that may be acquired fast enough to capture and resolve any intra-fraction organ motions that occur and result in significant changes in patient geometry while the dose from the radiation beams are being delivered. The data obtained by real-time imaging allows for the determination of the actual dose deposition in the patient. This is achieved by applying known techniques of deformable registration and interpolation to sum the doses delivered to the moving tissues and targets. This data taken over the entire multi-week course of radiotherapy, while the radiation beams are striking the patient and delivering the dose, allows for the quantitative determination of 3D in vivo dosimetry. Hence, the present invention enables the only effective means of assessing and controlling or eliminating organ motion related dose delivery errors.

SUMMARY OF THE INVENTION

The present invention provides a radiation treatment system including: at least one though possibly more radioisotopic sources to produce ionizing radiation treatment beams, at least one though possibly more MLC or attenuator systems to perform IMRT with the treatment beams; a magnetic resonance imaging (MRI) system that images the target region and surrounding healthy tissue or critical structures simultaneously during delivery of the ionizing radiation; and/or a controller communicably connected to all components. The image data derived from the MRI allows for the quantitative assessment of the actual delivered ionizing radiation dose and the ability to reoptimize or replan the treatment delivery to guide the ionizing radiation delivered by IMRT to the target region more accurately. We now describe a beneficial embodiment of the invention. In this beneficial embodiment, the main magnet Helmholtz coil pair of an open MRI is designed as a split solenoid so that the patient couch runs through a cylindrical bore in the middle of the magnets and the IMRT unit is aimed down the gap between the two selonoidal sections at the patient (FIG. 1 through FIG. 4). In this embodiment, the split solenoidal MRI (015) remains stationary while the shielded co-registered isotopic radiation source with a multi-leaf collimator IMRT unit (020) is rotated axially around the couch on the gantry (025) (note more than one (020) could be beneficially employed). The patient (035) is positioned on the patient couch (030) for simultaneous imaging and treatment. The co-registered isotopic radiation source (020) with a multi-leaf collimator contains a radioisotopic source (115) which is collimated with a fixed primary collimator (120), a secondary doubly divergent multileaf collimator (125), and tertiary multi-leaf collimator (130) to block interleaf leakage from the secondary multi-leaf collimator (125) (FIG. 5 through FIG. 7).

This embodiment is beneficial as it removes the need for rotating the open MRI to provide axial treatment beam access and it provides a magnetic field along the patient in the cranial-caudal direction, allowing for improved MRI speed using parallel multi-phased array RF transceiver coils for fast image acquisition.

We now describe additional beneficial embodiments of the process of this invention with varying complexity and computational demands. All of these process embodiments could employ any device embodiment. All such process embodiments may include the step of acquiring high resolution diagnostic quality volumetric MRI data before the daily delivery of radiation and then acquiring real-time MRI data during the radiation delivery where the real-time data may be collected on a different spatial grid or with a diminished signal-to-noise ratio to improve the speed of acquisition. One beneficial process embodiment would take the MRI data and apply methods known in the art for deformable image registration and dose calculation to the delivered IMRT cobalt unit fluences to determine the dose delivered to the target and critical structures during each delivery fraction. Corrections to the patient's treatment could then be taken to add or subtract delivery fractions to improve tumor control or reduce side effects, respectively. Along with the dosimetric assessment, the size and progression of the patient's disease would also be assessed on a daily basis.

A second beneficial process embodiment would take the MRI data and perform a reoptimization of the IMRT treatment plan before each single radiation delivery to improve the accuracy of the treatment delivery. This process would be combined with the previous process to assess the dose delivered to the target and critical structures during each delivery fraction.

A third beneficial process embodiment would take the MRI data and perform a reoptimization of the IMRT treatment plan on a beam-by-beam basis before the delivery of each radiation beam in a single radiation delivery to improve the accuracy of the treatment delivery. This process generally includes that the first process to be performed rapidly before each beam delivery.

A fourth beneficial process embodiment would take the MRI data and perform reoptimization of the IMRT treatment plan on a moment-by-moment basis during the delivery of each part of each radiation beam in a single radiation delivery to improve the accuracy of the treatment delivery. This process includes that the first process to be performed in real-time substantially simultaneously with the radiation delivery. The present invention contemplates the use of parallel computation employing many computers beneficially connected via a low latency local network or a secure connection on a wide area network may be used to greatly enhance the speed of the algorithms known in the art for MRI image reconstruction, deformable image registration, dose computation, and IMRT optimization.

In another aspect, the present invention also provides a method of applying radiotherapy, having the steps of determining a treatment plan for applying radiotherapy; obtaining images of a target region within a volume of a subject using a magnetic resonance imaging (MRI) system; irradiating the target and critical structure regions with a treatment beam, wherein the treatment beam treats the target region; and continuing to obtain images of the target and critical structure regions during irradiation of the target region; wherein the treatment plan may be altered during treatment based upon images of the target and critical structure regions obtained during treatment.

BRIEF DESCRIPTION OF DRAWINGS

There are shown in the drawings, embodiments which are presently contemplated, it being understood, however, that the invention is not limited to the precise arrangements and instrumentalities shown.

DETAILED DESCRIPTION OF THE INVENTION

Figure 1:
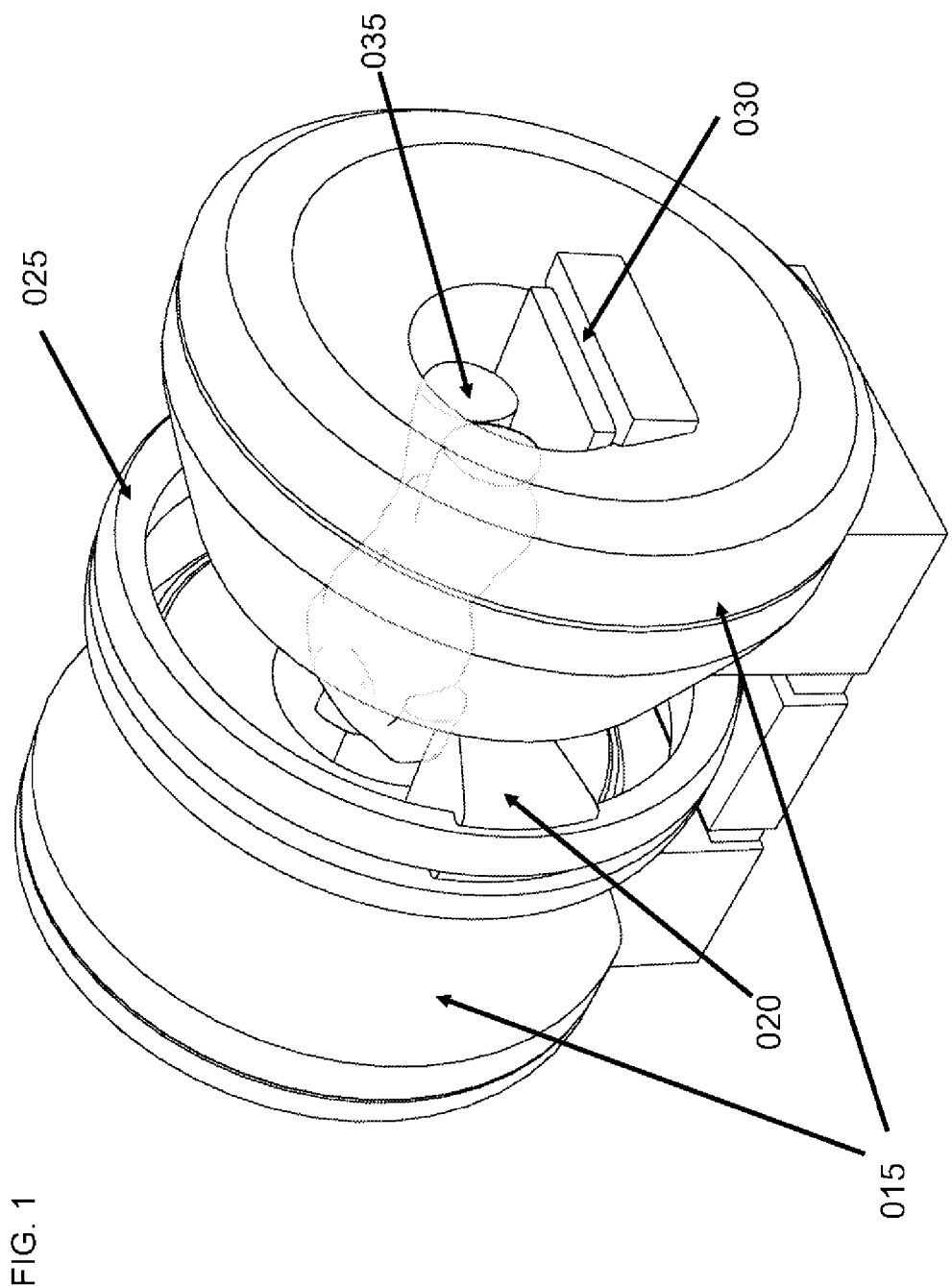
FIG. 1 is a schematic of a radiation therapy system including an open split solenoidal magnetic resonance imaging device (015), a shielded co-registered isotopic radiation source with a multi-leaf collimator (020) (note that more than one 020 could be applied in a beneficial embodiment), a gantry (025) for changing the angle of (020), a patient couch (030), and a patient (035) in position for simultaneous imaging and treatment.

The present invention is more particularly described in the following examples that are intended to be illustrative only since numerous modifications and variations therein will be apparent to those skilled in the art. As used in the specification and in the claims, the singular form "a," "an," and "the" may include plural referents unless the context clearly dictates otherwise. Also, as used in the specification and in the claims, the term "comprising" may include the embodiments "consisting of and "consisting essentially of."

The invention is both a device and a process for performing high temporal- and spatial-resolution magnetic resonance imaging (MRI) of the anatomy and disease of a patient during intensity modulated radiation therapy (IMRT) to directly measure and control the highly conformal ionizing radiation dose delivered to the patient. In a beneficial embodiment, this invention combines the technologies of an open MRI that allows for axial access with IMRT radiation beams to the patient, a multileaf-collimator or compensating filter-based IMRT delivery system, and cobalt-60 teletherapy radiation source or sources into a single co-registered and gantry mounted system.

As mentioned, the prior art does not simultaneously image the internal soft tissue anatomy of a person in real-time during the delivery of radiation therapy while the beams are striking the patient. Rather, an image is generated prior to and/or after the radiation delivery, and these images do not reflect any movement and/or natural changes that may occur in the patient during radiation delivery. As such, targeted radiation without the invention described here may not be successful if, after taking an initial image, the portion of the body to be treated either changes in size naturally, or changes in location due to the shifting of the patient prior to treatment; i.e., the occurrence of patient setup errors or errors in the geometry and alignment of the patients anatomy; physiological changes in the patient, such as weight loss or tumor growth and shrinkage; and organ motions in the patient including but not limited to breathing motion, cardiac motion, rectal distension, peristalsis, bladder filling, and voluntary muscular motion.

The present invention helps to eliminate all of these problems by performing real-time MRI of the patient substantially simultaneous to radiation delivery, and then readjusting the targeted radiation if the region to be treated suffers from any type of dosimetric error caused patient setup error, physiological change, and inter-fraction or intra-fraction organ motion. Many actions may be taken including, but not limited to: shifting the patient position to account for changes in size and/or position of targets and anatomy; stopping treatment altogether to permit additional calculations to be determined before restarting treatment or allow for the cessation of transitory motion; adding extra delivery fractions to increase the probability of tumor control or limiting the number of delivery fractions to decrease the probability of side effect; any of the beneficial process embodiments previous described; and reoptimizing the IMRT treatment plan on a variety of time scales, e.g., reoptimization for every delivery, every beam, or every segment in the IMRT plan is performed.

A beneficial embodiment of the present invention includes a computer controlled cone-beam cobalt therapy unit, such as a cobalt-60 therapy unit, equipped with a multileaf collimator or an automated compensating filter system mounted on a rotational gantry along with an orthogonally mounted "Open" MRI unit. As seen in FIG. 1, the IMRT cobalt unit (020) projects its cone-beam geometry radiation down the center of the opening of the axial open MRI unit (015) and the IMRT cobalt unit rotates axially (about the longitudinal (cranial-caudal) axis of the patient) about the patient on a gantry (025). An adjustable treatment couch (030) may be used to support the patient in a stationary position while the gantry rotates to change the beam angle.

The present invention uses cobalt teletherapy as the radiation therapy. While some IMRT uses a linear electron accelerator for delivering a more penetrating radiation therapy, the accelerator itself produces a treatment beam that is highly variable in regards to the level of radiation emitted. As such, it becomes difficult to accurately determine the amount of radiation that is being used on the patient and to coordinate the motion of an MLC for IMRT delivery. Gamma-rays are electromagnetic radiation emitted by the disintegration of a radioactive isotope and have enough energy to produce ionization in matter, typically from about 100 keV to well over 1 MeV. The most useful gamma-emitting radioactive isotopes for radiological purposes are found to be cobalt (Co 60), iridium (Ir 192), cesium (Cs 137), ytterbium (Yb 169), and thulium (Tm 170). As such, the disintegration of a radioactive isotope is a well-known phenomena and, therefore, the radiation emitted by cobalt teletherapy is more consistent and, therefore, easier to calculate in terms of preparing a treatment regimen for a patient.

Figure 8:
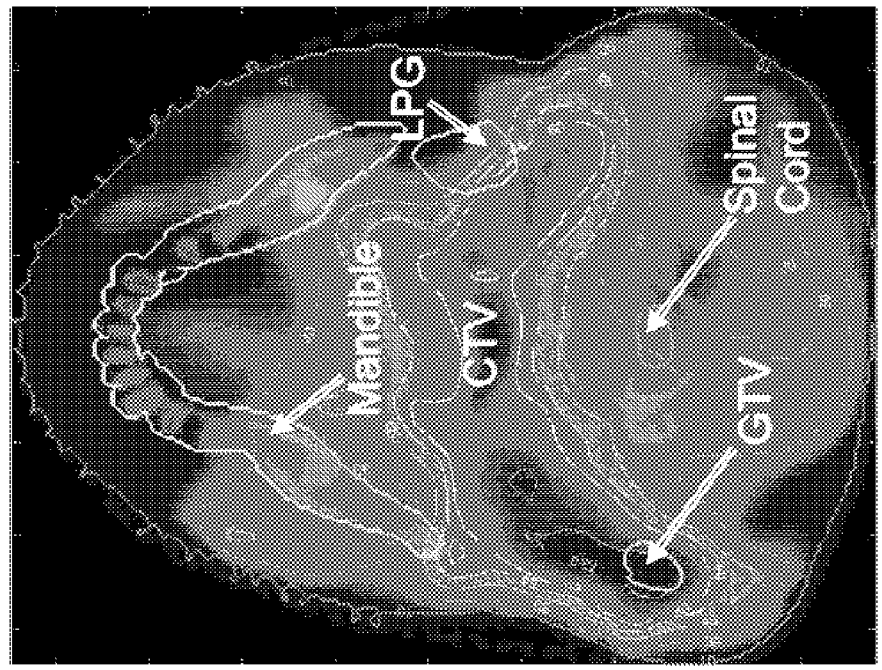
FIG. 8 displays axial dose distributions from the single head-and-neck IMRT case planned using the commissioned cobalt beamlets.
Figure 8:
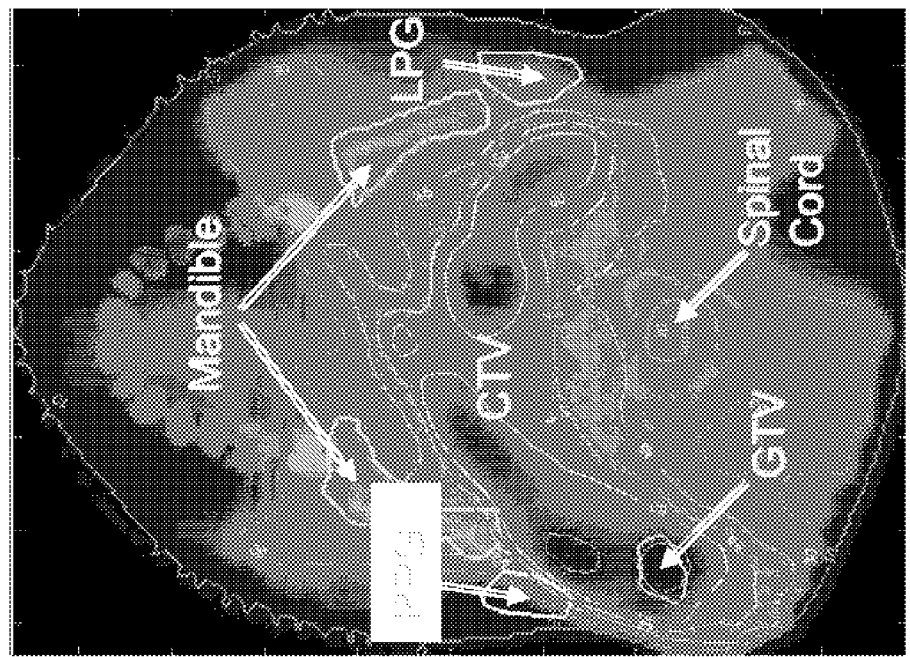
Figure 9:
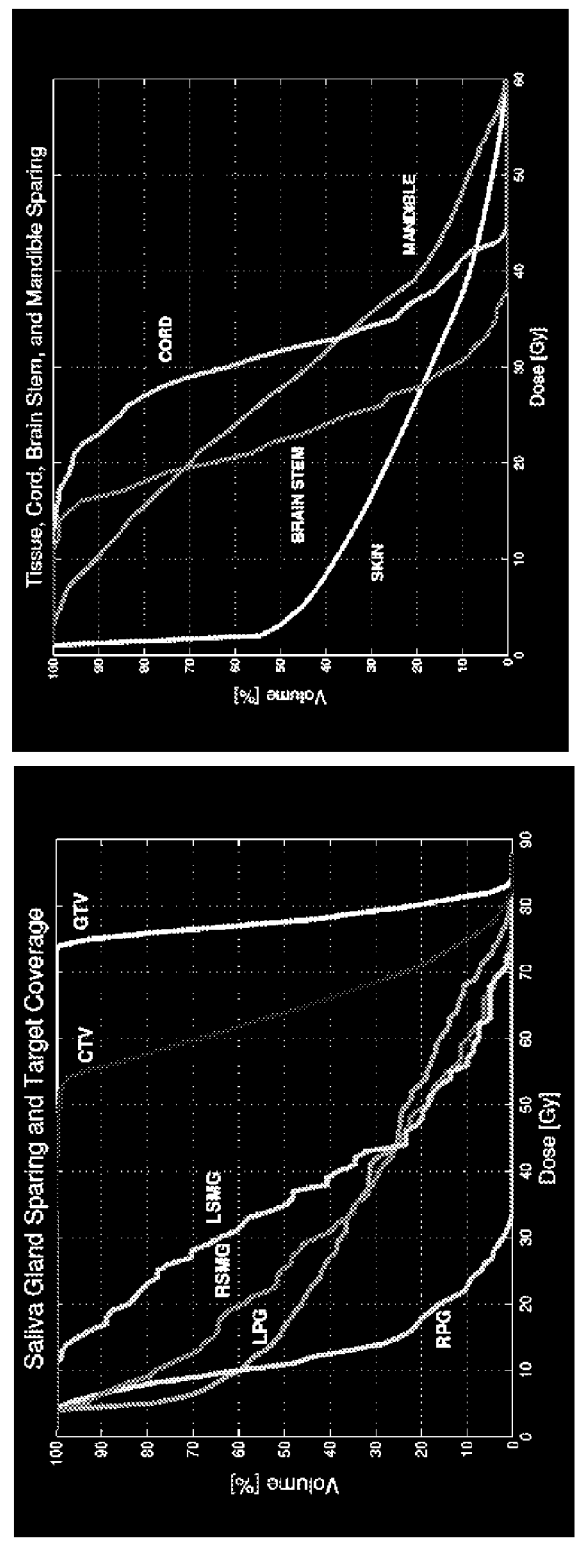
FIG. 9 displays the DVH data derived from the single head-and-neck IMRT case planned using the commissioned cobalt beamlets.

Enablement of the present invention's cobalt IMRT has been demonstrated via computational analysis. Simulations have been performed of IMRT delivery with a commercially available cobalt therapy unit and a MLC. A 3D image-based radiation therapy treatment planning system with a cobalt beamlet model was commissioned and validated using measured radiochromic film data from a Theratronics 1000C cobalt therapy unit. An isotropic 4×4×4 mm3 dose voxel grid (effectively Shannon-Nyquist limited for y-ray IMRT source penumbra) was generated. This beamlet model was fitted to published data and validated with radiochromic film measurements of 1×1 cm2 beamlets formed by a Cerrobend block and measured using a previously reported methodology. The calculation depths were then determined for the same voxels with standard three-dimensional ray-tracing of the structures. Density scaling to the depths computed was used to better account for tissue heterogeneities in the dose model. The CPLEX, ILOG Concert Technologies industrial optimization solver using an implementation of the barrier interior-point method with dense column handling for IMRT optimization was used to solve for optimal IMRT plans. Beamlet fluences were discretized for each beam angle to 5% levels for leaf sequencing. The resulting plan dose distribution and histograms were computed by summing the dose values weighted by the deliverable discretized intensities. Leaf-transmission leakage intensities were conservatively estimated at 1.7% for otherwise zero intensity beamlets. Finally, standard methods of heuristic leaf-sequencing optimization to create delivery instructions for the treatment plans were employed. We adopted the Virginia Medical College simultaneous integrated boost (SIB) target dose-level scheme as it is the largest maximum to minimum clinical prescription dose ratio advocated in the literature, making it the most difficult dose prescription scheme to satisfy. Head-and-neck IMRT provides an excellent basis for testing IMRT optimization for several reasons: 1) there are well defined treatment goals of sparing salivary glands and other structures while maintaining homogeneous target coverage; 2) attempting to achieve these goals tests IMRT optimization to its technical limits; and 3) a large phase I/II multi-institutional trial, the Radiation Therapy Oncology Group (RTOG)'s H-0022 Phase I/II Study of Conformal and Intensity Modulated Irradiation for Oropharyngeal Cancer, has defined a common set of planning criteria. The case examined was run with 7 equispaced beams having International Electrotechnical Commission (IEC) gantry angles of 0°, 51°, 103°, 154°, 206°, 257°, and 309°. The treatment planning system generated 1,289 beamlets to adequately cover the targets from the seven beam angles, and the 4 mm isotropic voxel grid generated 417,560 voxels. Results are shown in FIG. 8 and FIG. 9. Note that our system normalized plans to ensure 95% coverage of the high dose target. FIG. 8 displays axial dose distributions from the single head-and-neck IMRT case planned using the commissioned cobalt beamlets. Excellent target coverage and tissue sparing may be observed. FIG. 9 displays the DVH data derived from the leaf sequenced and leakage corrected plan (i.e., deliverable plan) using the 4 mm voxels and 1 Gy dose bins. The cobalt source based IMRT created an excellent IMRT treatment plan for a head-and-neck patient. The γ-ray IMRT was able to clearly spare the right parotid gland (RPG) and keep the left parotid (LPG) and right submandibular glands (RSMG) under 50% volume at 30 Gy, while covering more than 95% of the target volumes (CTV and GTV) with the prescription dose or higher. All other structures were below tolerance. The unspecified tissue (SKIN) was kept below 60 Gy, with less than 3% of the volume above 50 Gy. The optimization model used was the same as published in Romeijn et al. and was not modified for the cobalt beams. For sites with larger depths such as prostate and lung it is known in the art that the addition of extra beams or isocenters allows for the creation of treatment plans using cobalt IMRT that may achieve the same clinical quality criteria as linac-based IMRT. This enabling demonstration shows that a cobalt therapy unit is capable of providing high quality IMRT.

Figure 10:
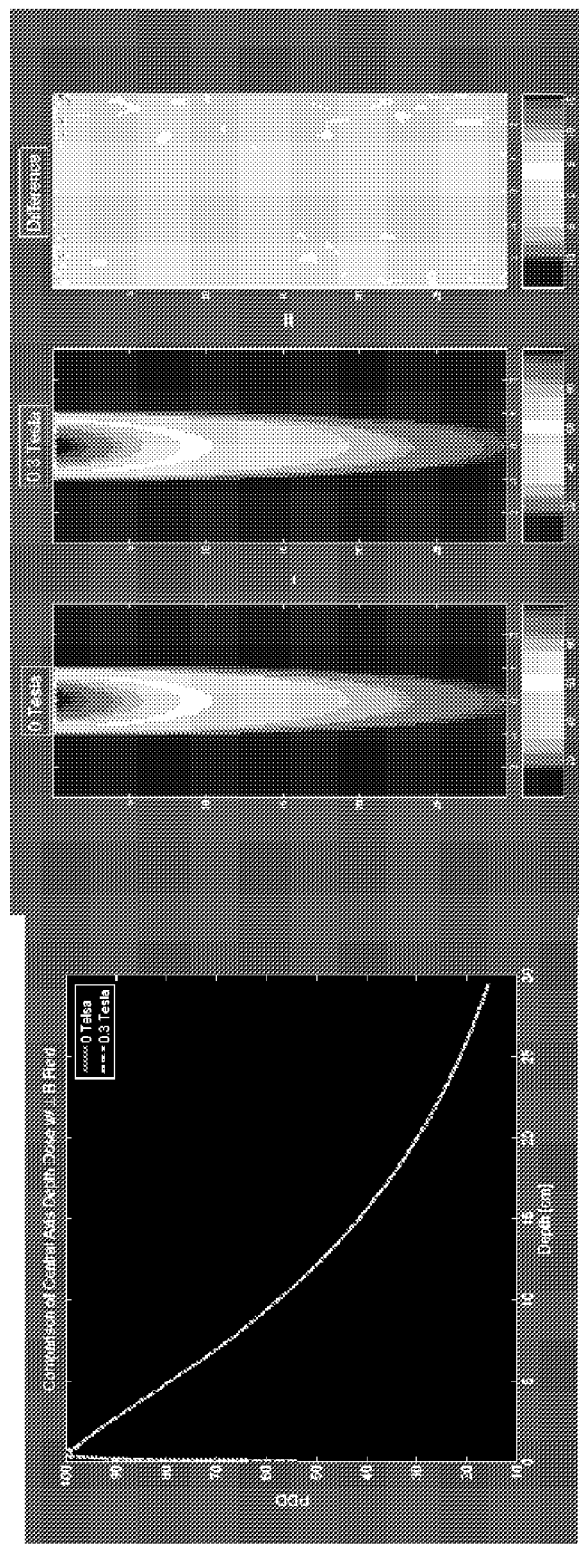
FIG. 10 cobalt beamlets dose distributions in water with and without a 0.3 Tesla magnetic field.
Figure 11:
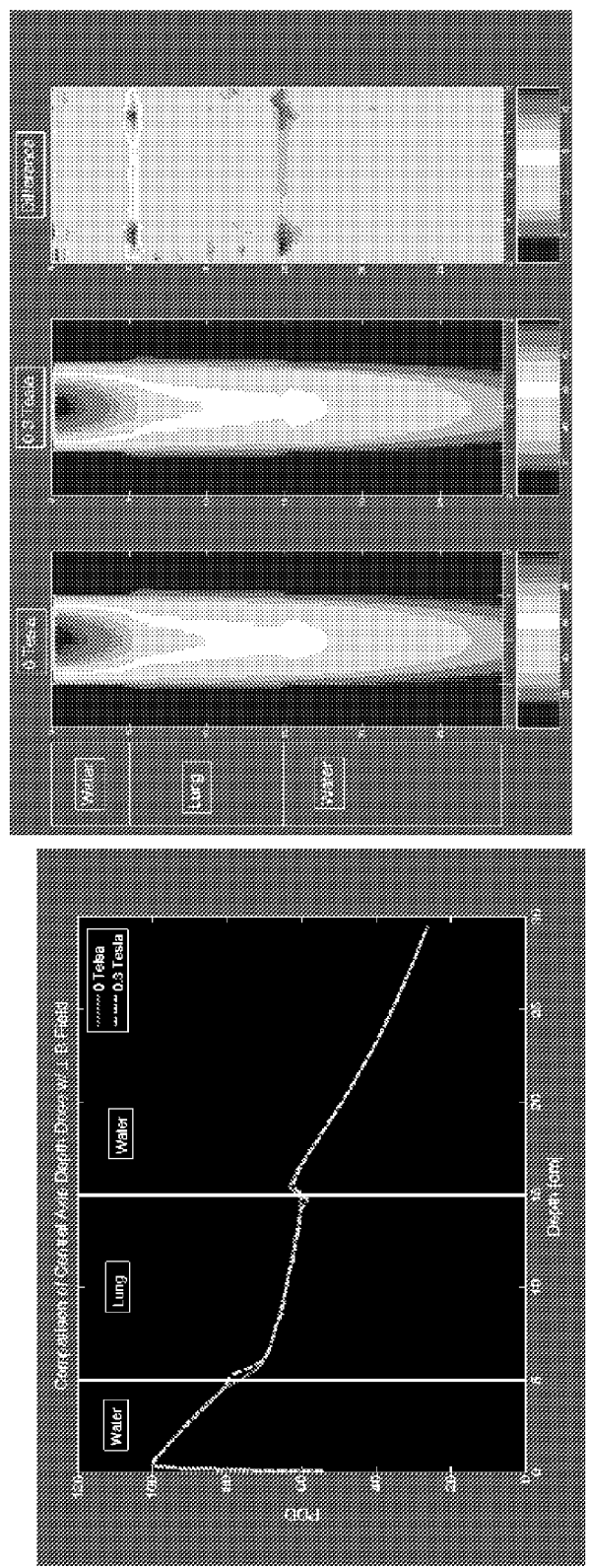
FIG. 11 cobalt beamlets dose distributions in water and lung with and without a 0.3 Tesla magnetic field.
Figure 12:
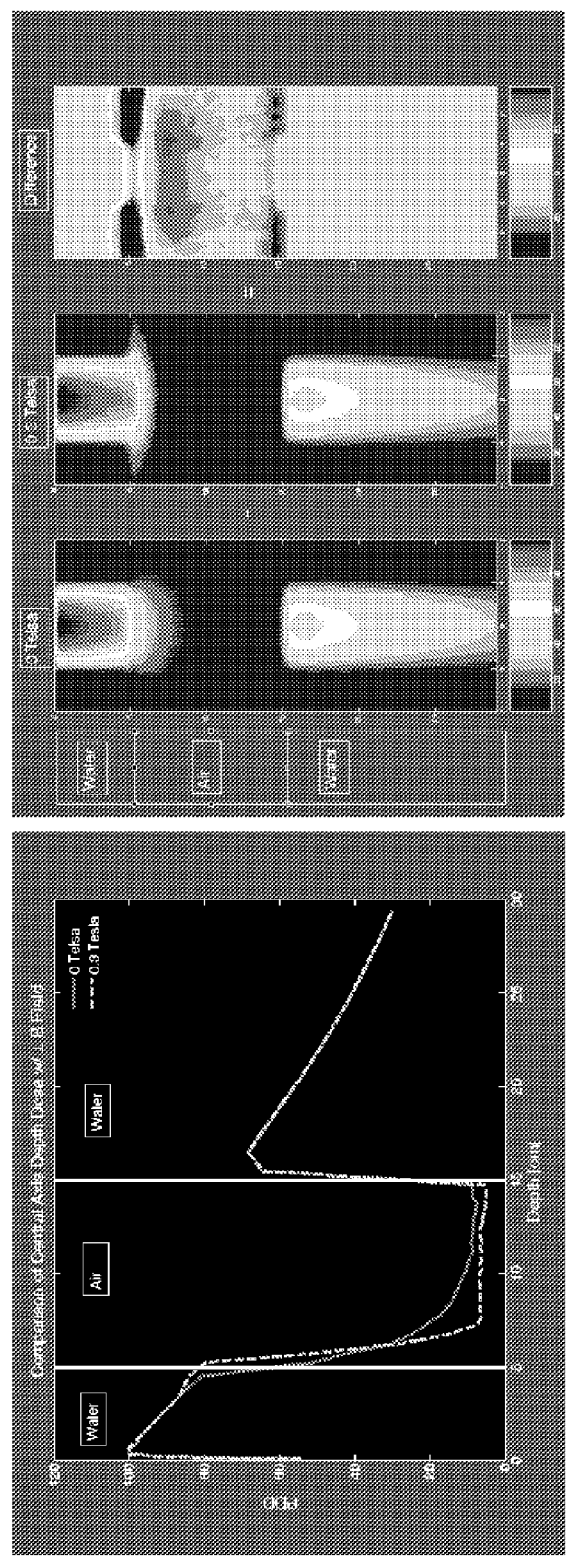
FIG. 12 cobalt beamlets dose distributions in water and air with and without a 0.3 Tesla magnetic field.

Enablement of the present invention's dose computation for cobalt IMRT in the presence of the magnetic field has been demonstrated via computational analysis. In addition, by using cobalt teletherapy, the present invention is better able to make calculations based upon the magnetic field of the MRI. When the radiation therapy is performed while the patient is stationed within the MRI, the magnetic field will cause a slight deflection of the targeted radiation. As such, the calculations used to determine the treatment regimen need to take this deflection into account. A charged particle moving in a vacuum at a velocity, $\overline{V}$, in the presence of a magnetic field, $\overline{B}$, experiences a Lorentz force given by $\overline{F}=q(\overline{v}\times\overline{B})$. This force is not significant enough to significantly change the physics of the interactions of ionizing photons and electrons with matter; however, it may influence the overall transport of ionizing electrons and hence the resulting dose distribution. The impact of magnetic fields on the transport of secondary electrons has been well studied in the physics literature, starting more than 50 years ago. Recent studies have employed Monte Carlo simulation and analytic analysis in an attempt to use a localized magnetic field to help focus or trap primary or secondary electrons to increase the local dose deposition in the patient. All of these studies have examined aligning the direction of the magnetic field lines along the direction of the beam axis to laterally confine the electron transport with the Lorentz force (called "longitudinal" magnetic fields, where the term longitudinal refers to the beam and not the patient). For high field MRI, with magnetic fields between about 1.5-3.0 T is known that the initial radius of gyration is small with respect to the MFP of large-angle scattering interactions for the secondary electrons (bremsstrahlung, elastic scatter, and hard collisions) and this condition results in the desired trapping or focusing of the electrons. As the electrons lose energy the radius decreases as it is proportional to $|\bar{v}|$ and, in the absence of large-angle scattering interactions (CSDA) the electrons would follow a spiral with decreasing radius until they stop. Although this spiraling may change the fluence of electrons it is known that it does not produce any significant synchrotron radiation. In the present invention, the magnetic field must be orthogonal to the radiation beams in order allow parallel MRI for real-time imaging. Recent work has shown that a 1.5 T magnetic field perpendicular to the beam axis of a 6 MV linac beam may significantly perturb the dose distribution to water for a 6 MV linac beamlet. Both to avoid such dose distribution distortions and to prevent MRI artifacts that could compromise the spatial integrity of the imaging data, a beneficial embodiment of the present invention uses a low field open MRI design that allows the magnetic field to be directed along the superior-inferior direction of the patient (see FIG. 1). Simple estimates of the radii of gyration for secondary electrons from cobalt γ rays indicate that the radii of gyration are much greater than the MFP for large-angle scattering interactions for electrons. This is easily understood as the Lorentz force is proportional to the magnitude of the magnetic field, $|\bar{B}|$ and the radius of gyration is inversely proportional to the magnetic field (104). We have pursued modeling a beamlet from a cobalt γ-ray source in a slab phantom geometry using the well-validated Integrated Tiger Series (ITS) Monte Carlo package and its ACCEPTM subroutine for transport in magnetic fields. For the simulations we employed 0.1 MeV electron and 0.01 MeV photon transport energy cutoffs, the standard condensed history energy grid (ETRAN approach), energy straggling sampled from Landau distributions, mass-collisional stopping powers based on Bethe theory, default electron transport substep sizes, and incoherent scattering including binding effect. Three pairs of simulations were run where each pair included the run with and without a 0.3 T uniform magnetic field parallel to the beam direction. A 2 cm circular cobalt γ-ray beamlet was modeled on the following geometries: a $30\times30\times30$ cm$^3$ water phantom; a $30\times30\times30$ cm$^3$ water phantom with a 10 cm lung density (0.2 g/cc) water slab at 5 cm depth; and a $30\times30\times30$ cm$^3$ water phantom with a 10 cm air density (0.002 g/cc) water slab at 5 cm depth. Simulations were run with between 30 and 100 million histories on a P4 1.7 GHz PC for between 8 and 30 hours to obtain less than a percent standard deviation in the estimated doses. The results are displayed in FIGS. 10-12. FIG. 10 clearly demonstrates that a 0.3 T perpendicular uniform magnetic field, as would exist in a beneficial embodiment of the current invention will not measurably perturb the dose distribution in soft tissue or bone. A very useful treatment site for the present invention will be lung and thorax which contains the most significant tissue heterogeneities in the body. As seen in FIG. 11, adding a 12 cm lung density (0.2 g/cc) water slab to the phantom causes a very small yet detectable perturbation in the dose at the interfaces of the high and low density regions. These perturbations are small enough to allow acceptable clinical application without correction. In FIG. 12, we finally observe significant perturbations, which exist largely in the low-density and interface regions. This demonstrates that air cavities will hold the greatest challenge for accurate dosimetry. However, other than at interfaces with lower density media there should be no significant perturbations in soft tissue and bone (where the MFP shortens even more than soft tissue). This data demonstrates that in a beneficial embodiment of the present invention with a low (0.2-0.5 Tesla) field MRI, dose perturbation will be small except inside of air cavities were accurate dosimetry is not required due to an absence of tissue. By using a known radiation source, such as a cobalt teletherapy unit, the amount of deflection may be easily determined if the strength of the MRI field is known. However, even if the strength of the field is known, if a linear accelerator is used, the unknown energy spectrum of the radiation makes the calculations much more difficult.

Alternate sources of radiation that do not interfere significantly with the operations of the MRI unit such as protons, heavy ions, and neutrons that are produced by an accelerator or reactor away from the MRI unit and transported by beam to patient are also included in the invention.

In addition, the strength of the MRI field will factor into the calculations and, as a result, the use of open MRIs offers advantages over closed MRIs. In an open MRI, the strength of the field generated is generally less than the field of a closed MRI. As such, the images resulting from an open MRI have more noise and are not as clear and/or defined as images from a higher field closed MRI. However, the stronger field of the closed MRI causes more of a deflection of the radiation treatment than the weaker field of an open MRI. Accordingly, depending on the characteristics most beneficial to a given treatment regimen, the present invention contemplates that a closed MRI could be used. However, due to ease of calculation and/or the fact that a slightly less clear image during treatment is sufficient for adjusting most treatment regimens, the present invention contemplates that an open MRI of the geometry shown in FIG. 1, is used with the cobalt teletherapy to eliminate significant dose perturbations, prevent spatial imaging distortions, and allow for fast parallel phased array MRI.

By using an open MRI and cobalt teletherapy, the present invention provides three dimensional (3D) imaging of a patient during the radiation therapy. As such, by using the 3D images of the target region and the planning images of the target region a displacement is determined which is updated based upon the continuous 3D images received during the radiotherapy process. Using the information obtained, the patient may then be then translated relative to the treatment beam to reduce the displacement during the irradiation process, such as if the measured displacement is outside a predetermined limit. Irradiation may then continue after translation. Alternatively, the treatment beam may be moved. The translation may occur during treatment or treatment may be stopped and then translation may occur.

By using 3D images during treatment and using these images to rapidly position and/or adjust the patient during the radiotherapy process, treatment accuracy may be substantially improved. If the patient becomes misaligned while radiation is being applied, the misalignment may be mitigated through positional adjustment. In addition to possible dose escalation, improved positional accuracy permits treatment of tumors that are currently considered not treatable with radiation using conventional systems. For example, primary spinal cord tumors and spinal cord metastases are typically not treated by conventional radiation systems due to the high accuracy needed to treat lesions in such important functional anatomic regions. The increased precision provided by 3D imaging during treatment makes it feasible to treat these types of tumors. Improvements are also expected for targets located in the lung, upper thorax, and other regions where intra-fraction organ motions are known to cause problems with radiotherapy dosimetry.

In an alternative embodiment, the present invention may include a separate guidance system to track the patient location that may be used to correlate the actual patient position with the imaging information obtained during both planning and radiotherapy. This portion of the invention may significantly improve the ease of patient positioning by providing updateable image correlation and positioning information throughout the patient set-up and treatment delivery phases, even when the patient is moved to positions that are not perpendicular to the coordinate system of the therapy machine. This ability to monitor patient position at non-coplanar treatment positions may be a significant improvement over conventional radiotherapy systems. In one beneficial embodiment, the guidance system may include an adjustable bed or couch for the patient to be placed upon. In an alternative beneficial embodiment, the guidance system may include a gantry that permits substantially simultaneous movement of the MRI and the cobalt therapy unit. Some beneficial embodiments include both the gantry and the adjustable bed or couch.

The present invention determines the initial radiation treatment and/or any changes to the treatment regimen based upon the use of a computer program that takes into account various factors including, but not limited to, the area of the patient to be treated, the strength of the radiation, the strength of the MRI field, the position of the patient relative to the radiation unit, any change in the patient during treatment, and/or any positional changes necessary of the patient and/or the radiation unit during treatment. The resulting IMRT is then programmed and the treatment is started.

One embodiment for determining a treatment plan for intensity modulated radiation treatment (IMRT) as used in the present invention includes the steps of dividing a three dimensional volume of a patient into a grid of dose voxels, wherein each dose voxel is to receive a prescribed dose of radiation from a plurality of beamlets each having a beamlet intensity; and providing a convex programming model with a convex objective function to optimize radiation delivery. The model is solved to obtain a globally optimal fluence map, the fluence map including beamlet intensities for each of the plurality of beamlets. This method is described in greater detail in related application U.F. Disclosure No. 11296.

In general, the method used for determining a treatment plan, in one beneficial embodiment, is the interior point method and variants thereof. This method is beneficial due to its high efficiency and resulting generally short computational times. The interior point method is described in a book by Steven J. Wright entitled "Primal-Dual Interior-Point Methods" (SIAM, Publications, 1997, ISBN 089871382X). Primal-dual algorithms have emerged as the most beneficial and useful algorithms from the interior-point class. Wright discloses the major primal-dual algorithms for linear programming, including path-following algorithms (short- and long-step, predictor-corrector), potential-reduction algorithms, and infeasible-interior-point algorithms.

Once the treatment plan is determined, the present invention enables the clinician to ensure that the treatment plan is followed. The patient to be treated is placed in the MRI. An image of the area to be treated is taken and the MRI continues to transmit a 3D image of the area. The treatment plan is input into the cobalt radiation teletherapy unit and treatment commences. During treatment, a continuous image of the area being treated is observed. If the location of the area to be treated changes, such as if the patient moves or the area to be treated changes in size, the present invention either recalculates the treatment plan and/or adjusts the patient or radiation unit without interrupting treatment; or the present invention stops treatment, recalculates the treatment plan, adjusts the patient and/or adjusts the radiation unit before recommencing treatment.

The present invention contemplates multiple process embodiments that may be used in improving the accuracy of the patient's therapy. One process embodiment would take the MRI data and apply methods known in the art for deformable image registration and dose calculation to the delivered IMRT cobalt unit fluences to determine the dose delivered to the target and critical structures during each delivery fraction. Corrections to the patient's treatment could then be taken to add or subtract delivery fractions to improve tumor control or reduce side effects, respectively. Along with the dosimetric assessment, the size and progression of the patient's disease would also be assessed on a daily basis.

A second process embodiment would take the MRI data and perform a reoptimization of the IMRT treatment plan before each single radiation delivery to improve the accuracy of the treatment delivery. This process would be combined with the previous process to assess the dose delivered to the target and critical structures during each delivery fraction.

A third process embodiment would take the MRI data and perform a reoptimization of the IMRT treatment plan on a beam-by-beam basis before the delivery of each radiation beam in a single radiation delivery to improve the accuracy of the treatment delivery. This process includes that the first process be performed rapidly before each beam delivery.

A fourth process embodiment would take the MRI data and perform reoptimization of the IMRT treatment plan on a moment-by-moment basis during the delivery of each part of each radiation beam in a single radiation delivery to improve the accuracy of the treatment delivery. This process also includes that the first process be performed in real-time simultaneously with the radiation delivery. The present invention contemplates the use of parallel computation employing many computers beneficially connected via a low latency local network or a secure connection on a wide area network may be used to greatly enhance the speed of the algorithms known in the art for MRI image reconstruction, deformable image registration, dose computation, and IMRT optimization.

Reference is now made with specific detail to the drawings in which like reference numerals designate like or equivalent elements throughout the several views, and initially to FIG. 1.

In FIG. 1, the present invention, in one embodiment, shows the system of the present invention and having an open MRI 015 and an IMRT cobalt therapy unit 020. The system also includes a means to perform IMRT in 020, such as an MLC or compensation filter unit, and a gantry 025 that may be used for cobalt unit 020 rotation while keeping the MRI 015 stationary. The patient 035 is positioned in the system on an adjustable, stationary couch 030.

Figure 2:
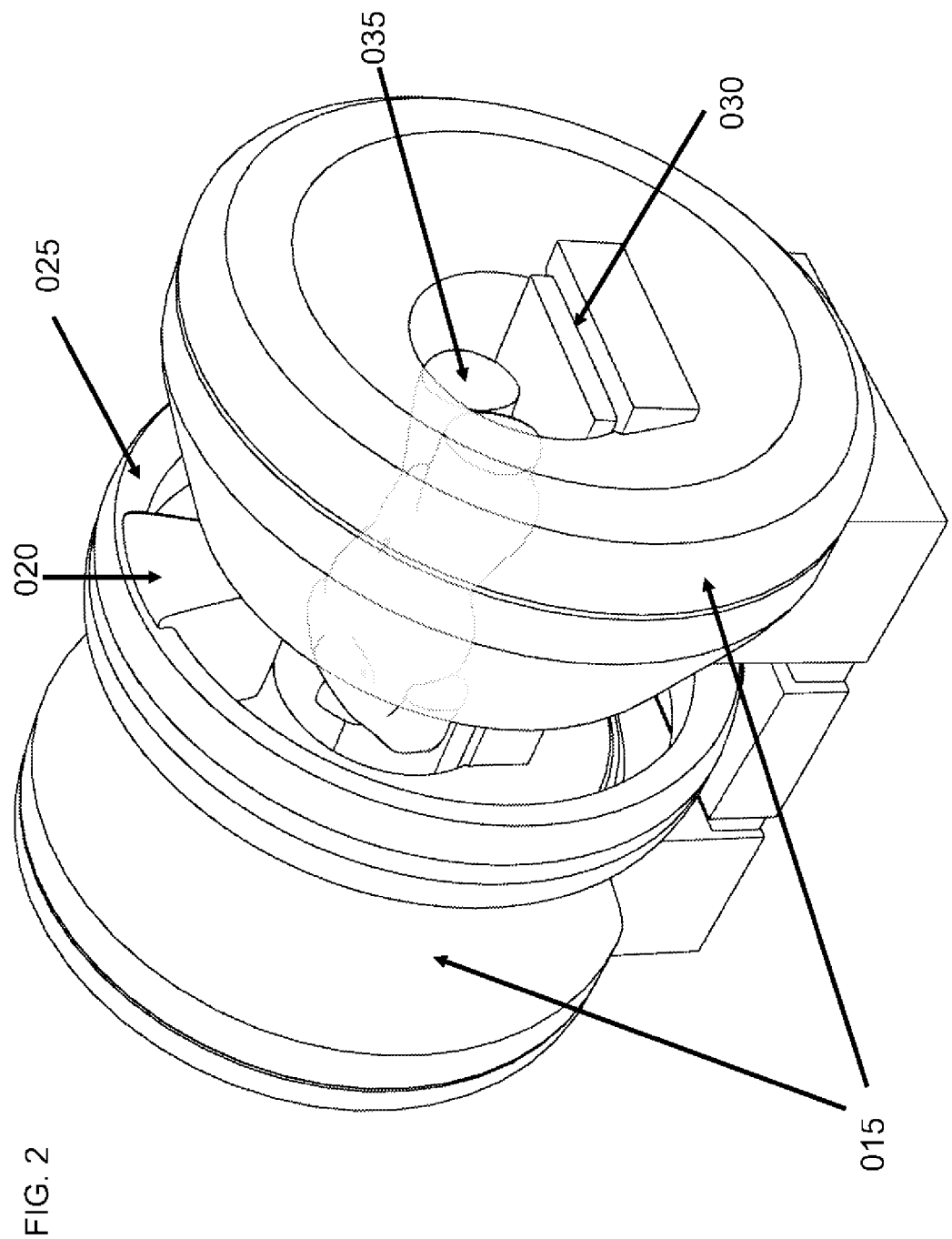
FIG. 2 is a demonstration of gantry rotation, where the shielded co-registered isotopic radiation source with a multi-leaf collimator (020), has been rotated from a right lateral beam position to an anterior-posterior beam position.

FIG. 2 shows the system in use and wherein the gantry 025 has been rotated approximately 90 degrees clockwise.

Figure 3:
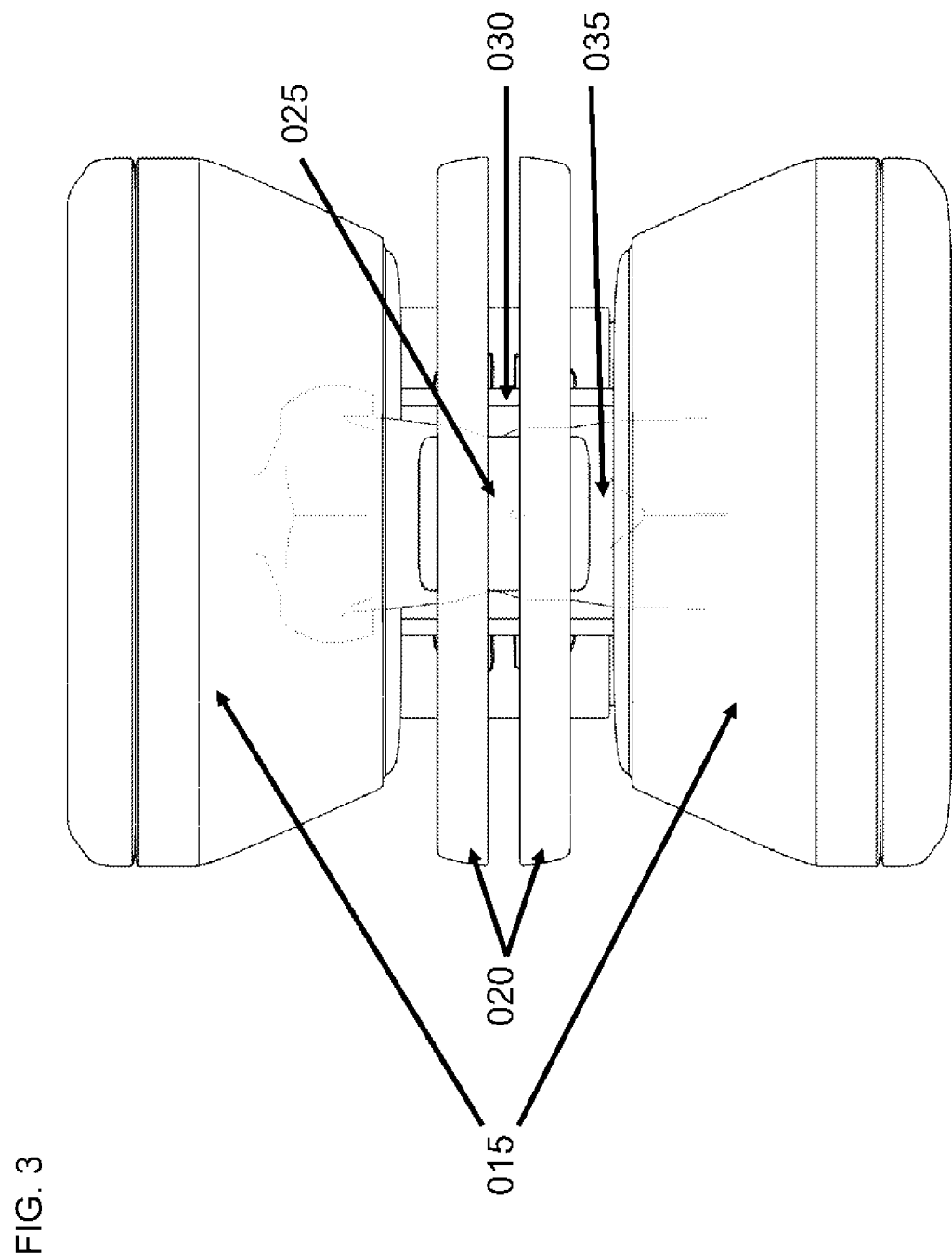
FIG. 3 is a top view of the system in FIG. 1.
Figure 4:
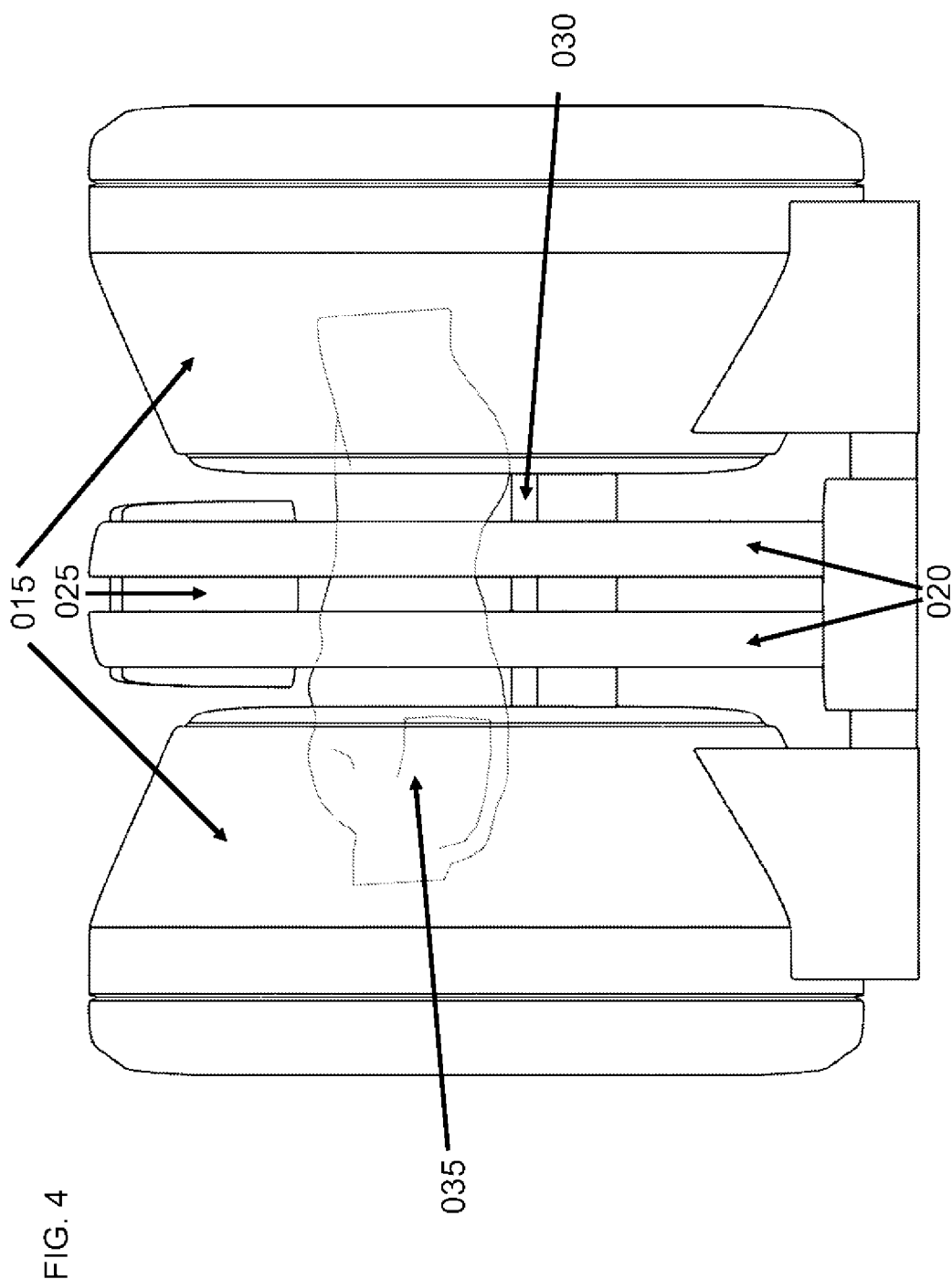
FIG. 4 is a side view of the system in FIG. 1.
Figure 5:
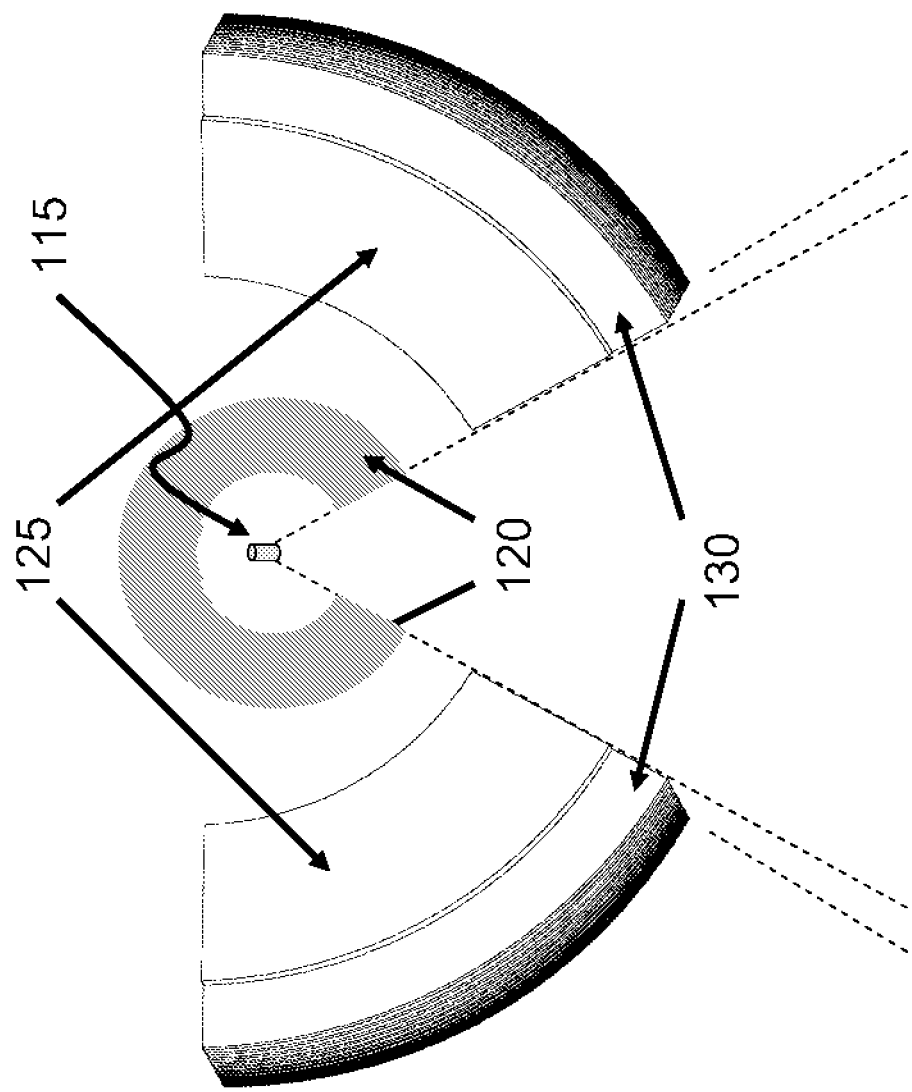
FIG. 5 is a detailed schematic of the co-registered isotopic radiation source with a multi-leaf collimator shown as (020) in FIG. 1. A radioisotopic source (115), is shown with a fixed primary collimator (120), a secondary doubly divergent multileaf collimator (125), and tertiary multi-leaf collimator (130) to block interleaf leakage from the secondary multi-leaf collimator (125).
Figure 6:
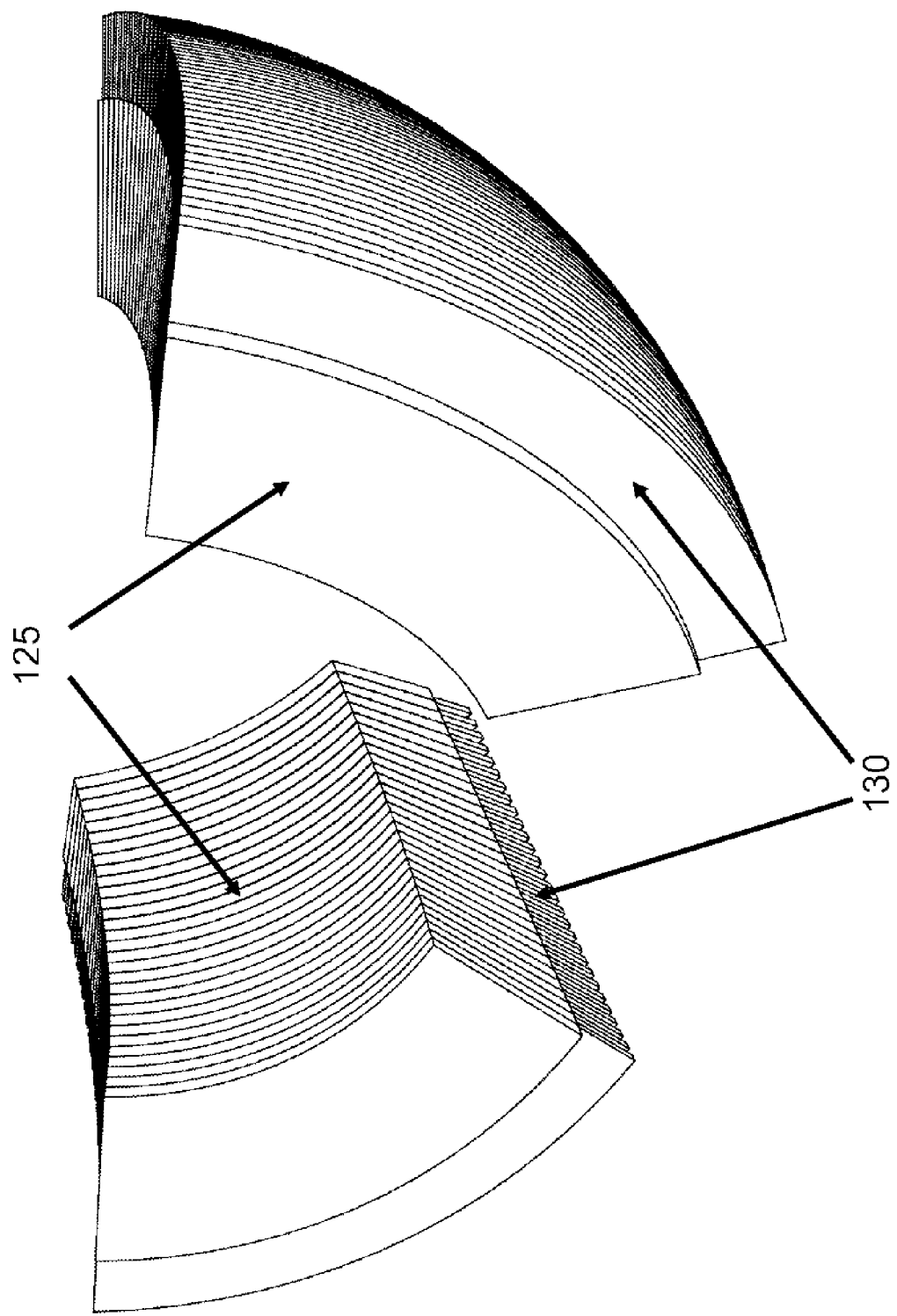
FIG. 6 is a perspective view of the secondary doubly divergent multi-leaf collimator (125), and the tertiary multi-leaf collimator (130) to block interleaf leakage from the secondary multi-leaf collimator (125).
Figure 7:
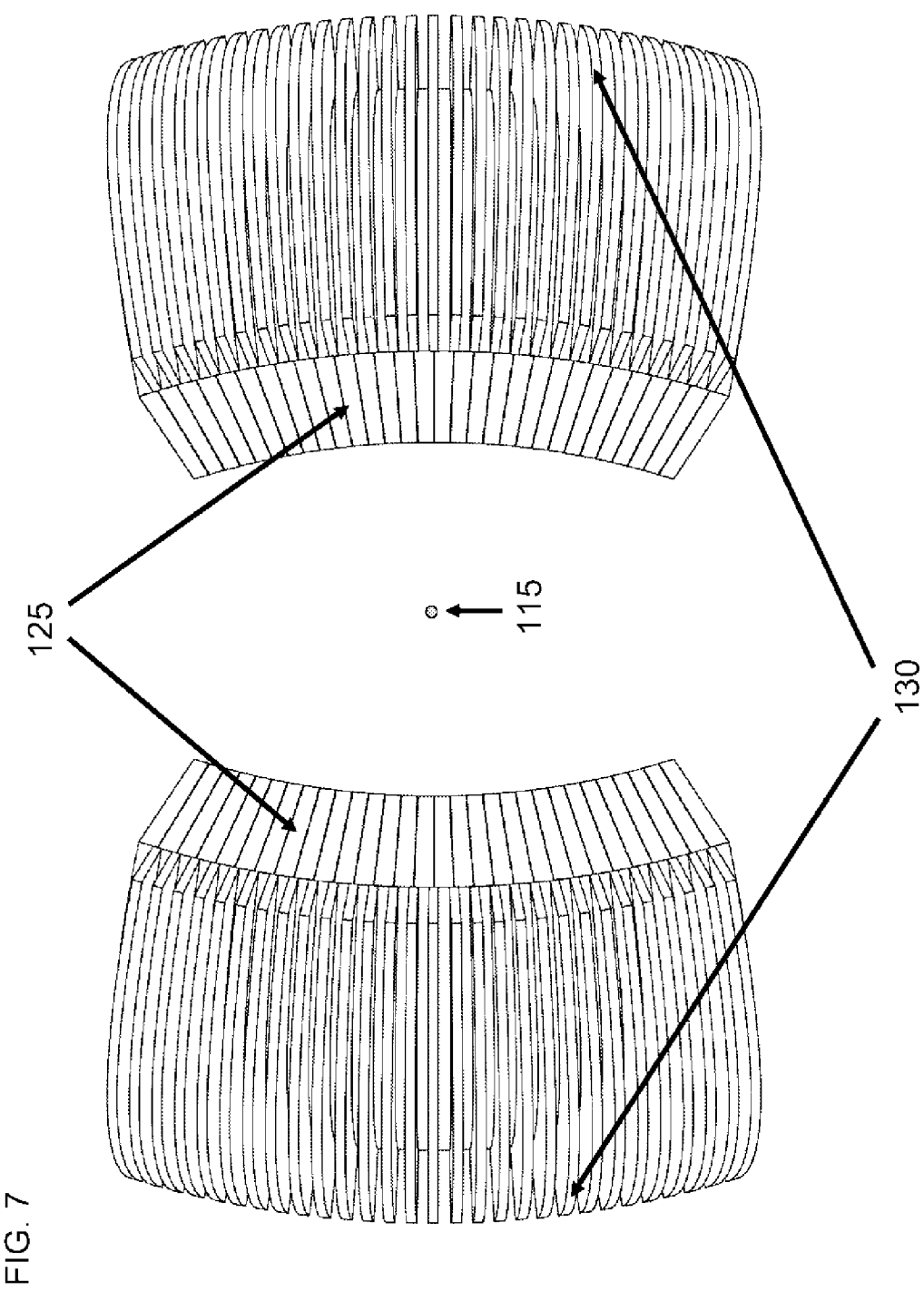
FIG. 7 is a beams-eye view of the radioisotopic source (115), the secondary doubly divergent multi-leaf collimator (125), and the tertiary multi-leaf collimator (130) to block interleaf leakage from the secondary multi-leaf collimator (125).

As such, the cobalt therapy unit 020 is in position to treat the patient 035 in one of many selected locations. FIG. 3 is a top view of the system in FIG. 1. FIG. 4 is a side view of the system in FIG. 1.

Although the illustrative embodiments of the present disclosure have been described herein with reference to the accompanying drawings and examples, it is to be understood that the disclosure is not limited to those precise embodiments, and various other changes and modifications may be affected therein by one skilled in the art without departing from the scope of spirit of the disclosure. All such changes and modifications are intended to be included within the scope of the disclosure as defined by the appended claims.

The invention claimed is:

1. A computer program product comprising a non-transitory machine-readable medium storing instructions that, when executed by at least one programmable processor, cause the at least one programmable processor to perform operations comprising:
   receiving magnetic resonance imaging data captured by a magnetic resonance imaging system during radiation therapy of a patient during a treatment fraction, the magnetic resonance imaging data acquired at a rate sufficient to capture intra-fraction organ motions;
   receiving data indicating ionizing radiation doses delivered to the patient; and
   determining an actual dose deposition in the patient from the magnetic resonance imaging data and the delivered ionizing radiation doses data by summing doses delivered to the patient over at least a portion of the treatment fraction.

2. The computer program product of claim 1 further comprising determining a reoptimized treatment plan based on the determined actual dose deposition.

3. The computer program product of claim 1 further comprising determining a reoptimized intensity modulated radiation therapy plan based on the determined actual dose deposition.

4. The computer program product of claim 1, wherein the data indicating ionizing radiation doses delivered to the patient is in the form of delivered fluences.

5. The computer program product of claim 1, wherein the data indicating ionizing radiation doses delivered to the patient is in the form of delivered cobalt fluences.

6. The computer program product of claim 1, wherein the magnetic resonance imaging data comprises three dimensional data.

7. A system comprising:
   a multileaf collimator configured for attenuation of a beam delivering ionizing radiation to a patient during a treatment fraction, the patient having moving tissues during the treatment fraction;
   a magnetic resonance imaging system configured to acquire magnetic resonance imaging data of patient anatomy fast enough to capture intra-fraction organ motion during the treatment fraction; and
   a controller configured to determine an actual dose deposition in the patient from the magnetic resonance imaging data and the delivered ionizing radiation by summing doses delivered to the moving tissues of the patient over at least a portion of the treatment fraction.

8. The system of claim 7, wherein the controller is further configured to reoptimize a treatment plan based on the determined actual dose deposition.

9. The system of claim 7, wherein the controller is further configured to stop the delivery of ionizing radiation if the actual dose deposition evidences a dosimetric error.

10. The system of claim 7, wherein the controller and multileaf collimator are configured to rapidly adjust the multileaf collimator to account for intra-fraction organ motions.

11. The system of claim 7, wherein the magnetic resonance imaging system is further configured to monitor the patient's response to therapy during the treatment fraction.

12. The system of claim 7, wherein the magnetic resonance imaging system is configured to operate at a field strength below 1.0 T.

13. The system of claim 7, wherein the magnetic resonance imaging system is configured to operate at a field strength of between 0.2 and 0.5 T.

14. The system of claim 7, wherein the magnetic resonance imaging data comprises three dimensional data.

\* \* \* \* \*